United States Patent [19]

Suyama et al.

[11] 4,196,151
[45] Apr. 1, 1980

[54] PROCESS FOR PRODUCING β,γ-UNSATURATED ALDEHYDE

[75] Inventors: Shuji Suyama, Aichi; Mamoru Shimizu, Tokoname, both of Japan

[73] Assignee: Nippon Oil and Fats Co., Ltd., Tokyo, Japan

[21] Appl. No.: 904,473

[22] Filed: May 10, 1978

[30] Foreign Application Priority Data

May 14, 1977 [JP] Japan .................................. 52/55838

[51] Int. Cl.² ............................................. C07C 47/20
[52] U.S. Cl. ................................................ 260/601 R
[58] Field of Search .................................... 260/601 R

[56] References Cited

U.S. PATENT DOCUMENTS 4,010,270   3/1977   Hall et al. ......................... 260/601 R

OTHER PUBLICATIONS

Dietl et al., "Tetrahedron Letter", No. 15, pp. 1273–1275, (1973).

Primary Examiner—Warren B. Lone
Attorney, Agent, or Firm—Blanchard, Flynn, Thiel, Boutell & Tanis

[57] ABSTRACT

Two molecules of mono-substituted acetaldehyde having the following general formula (I) and one molecule of organic halide having the following general formula (II) are reacted in an alkaline aqueous solution in the presence of a phase transfer catalyst whereby a β-γ-unsaturated aldehyde having the general formula (III) as shown in the following reaction scheme (A) is obtained directly from the monosubstituted acetaldehyde without forming an α,β-unsaturated aldehyde

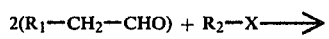

(I)        (II)

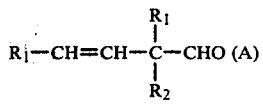

(III)

wherein $R_1$ is straight chain or branched chain alkyl, alkenyl, cycloalkyl or aryl, $R_2$ is allyl, substituted allyl, propargyl, substituted propargyl, benzyl or substituted benzyl, and X is halogen.

11 Claims, No Drawings

PROCESS FOR PRODUCING β,γ-UNSATURATED ALDEHYDE

BACKGROUND OF THE INVENTION

The present invention relates to a process for producing β,γ-unsaturated aldehydes having the following formula.

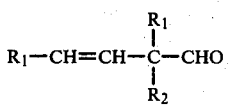

wherein $R_1$ is straight chain or branched chain alkyl, alkenyl, cycloalkyl or aryl, and $R_2$ is allyl, substituted allyl, propargyl, substituted propargyl, benzyl or substituted benzyl.

Unsaturated aldehydes are generally used in many fields and especially they are valuable substances as fundamental materials for food flavoring and perfume compositions etc. and as intermediates for the preparation of pharmaceutical substances and organic synthetic compounds. Among the unsaturated aldehydes, those aldehydes having the double bond between the α- and β carbon atoms are easily obtained by aldol condensation reaction of saturated aldehydes or dehydrating reaction of the resulting condensate. However, although unsaturated aldehydes having the double bond between the β- and γ carbon atoms having peculiar properties in comparison with those having the double bond between the α- and β- carbon atoms, their uses have been limited since there has not existed a simple method for producing them.

DESCRIPTION OF THE PRIOR ART

S. A. G. de Graff et al. report in Tetrahedron Letters No. 17 PP 1653-56, 1974, that α,β-unsaturated aldehyde (1-cyclohexene carboxyaldehyde or 2-methyl-2-pentene -1-al) could be converted into α,γ-unsaturated aldehyde by reaction with a small excess of potassium amide in liquid ammonia at −60° C. using reactive alkylating agents.

John B. Hall et al. disclose in U.S. Pat. No. 4,010,207 that β,γ-unsaturated aldehydes could be obtained from α,β-unsaturated aldehydes by the reaction shown in the following reaction scheme using a phase transfer agent

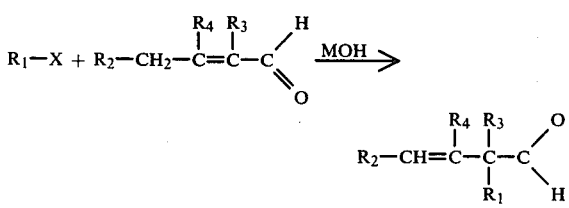

wherein $R_1$ is allyl or benzyl, $R_2$ is alkyl, aryl, alkenyl or alkoxyalkyl and $R_3$ and $R_4$ are each hydrogen or alkyl.

However, the above mentioned processes use an α,γ-unsaturated aldehyde as a starting material for obtaining a β,γ-unsaturated aldehyde. Accordingly, these processes at first need to convert a mono-substituted acetaldehyde into an α,γ-unsaturated aldehyde by a conventional method of aldol condensation and further need to convert the thus obtained product into the final intermediate product after separating and purifying the same.

Accordingly, the conventional methods require two procedures each of which comprises the steps of reacting, separating and drying in order to obtain the final product with the result being that the methods are complicated and the yield is decreased owing to the handling losses and occurrence of the by-products.

SUMMARY OF THE INVENTION

It is a main object of the invention to provide a new process for producing β,γ-unsaturated aldehydes from mono-substituted acetaldehydes and organic halide directly by a one step reaction.

It is another object of the invention to provide a new process for producing β,γ-unsaturated aldehydes in good yield, in a short time and in which the handling losses of the starting material are small. The present invention is based on the knowledge that when a mono-substituted acetaldehyde and an organic halide are reacted in alkaline aqueous solution in the presence of a phase transfer catalyst, a β,γ-unsaturated aldehyde can be obtained directly without accompanying by-products.

Namely, the present invention is characterized in that two molecules of mono-substituted acetaldehyde having the following general formula (I) and one molecule of organic halide having the following general formula (II) are reacted in alkaline aqueous solution in the presence of a phase transfer catalyst whereby a β,γ-unsaturated aldehyde having the general formula (III) as shown in the following reaction scheme (A) is obtained

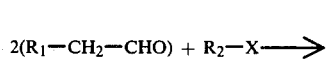

(I)      (II)

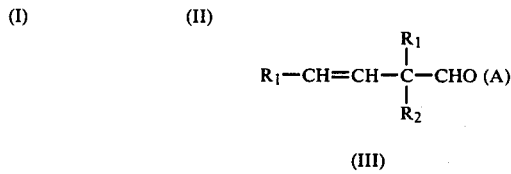

(III)

wherein $R_1$ is straight chain or branched chain alkyl, alkenyl, cycloalkyl or aryl, $R_2$ is allyl, substituted allyl, propargyl, substituted propargyl, benzyl or substituted benzyl and X is halogen.

Illustrative of the mono-substituted acetaldehydes are propionaldehyde, butyraldehyde, valeraldehyde, isovaleraldehyde, n-caproaldehyde, heptylaldehyde, caprylaldehyde, pelargonealdehyde, capricaldehyde, undecylaldehyde, laurylaldehyde, tridecylaldehyde, tetradecylaldehyde, phenylacetaldehyde, substituted-phenylacetaldehyde, citronellal, undecylenealdehyde and cyclohexylacetaldehyde. An aldehyde having no hydrogen atom at the α carbon atom is not converted into the β, γ unsaturated aldehyde, since said aldehyde does not give rise to aldol condensation reaction.

Further, an aldehyde which has one hydrogen at the α carbon atom is reacted with a organic halide before the aldol condensation reaction takes place. Accordingly these mentioned aldehydes could not be adapted to the present invention.

As the organic halides used for the present invention, there are mentioned compounds such as allyl chloride, crotyl chloride, methallyl chloride, 2-methylcrotyl chloride, prenyl chloride, 2,-3,-dimethylcrotyl chloride, 2-heptenyl chloride, 4,4-dimethyl-2-pentenyl chloride. 2-chlorolallyl chloride, 3-chloroallyl chloride, 2-bromoalyl chloride, 2-methyl-3-chloroallyl chloride, 1,3-dichloropentene-2, cinnamyl chloride, geranyl chloride, 3-chloropropyne, 1-chloro-2-butyne, 3-chloro-1-butyne, 1-1-chloro-2-pentyne, 1-chloro-2-hexyne, 1-chloro-2-heptyne, 1-phenyl-3-chloropropyne, 1,4-dichloro-2-butyne, benzyl chloride, ortho-, metha-, and para-monosubstituted benzyl chlorides, and di-, tri- and tetra-substituted benzyl chlorides such as methyl-substituted benzyl chloride, ethyl-substituted benzyl chloride, isopropyl benzyl chloride, fluoro-substituted benzyl chloride, chloro-substituted benzyl chloride, bromo-substituted benzyl chloride, iodo-substituted benzyl chloride, hydroxy-substituted benzyl chloride, methoxy-substituted benzyl chloride, phenoxy-substituted benzyl chloride, nitro-substituted benzyl chloride, cyan-substituted benzyl chloride, acetyl-substituted benzyl chloride, α-chloromethylnaphthalene and compounds which are substituted with other halogen atom in place of the chlorine atom positioned at X in the formula (II) $R_2$—X of the above mentioned components.

The reaction mechanism of the present invention is not clear but it is presumed that 2 molecules of the formula (I) aldehyde undergo aldol condensation thus obtaining the resultant intermediate compound (hereinafter called the aldehyde dimer) and the aldehyde dimer is reacted with an organic halide whereby the $\beta,\gamma$-unsaturated aldehyde is obtained.

Accordingly, the formula (I) aldehydes are used in an amount of two moles per one mole of the organic halide.

It is practical for the production to use the aldehyde and the organic halide in the range of 2–10 moles of the former to one mole of the latter.

The phase transfer catalyst used in the invention mean the ones having the function and effects as described in paragraph of "phase transfer catalyst" in Journal of the chemical society, of Japan, Chemistry and Chemical Industry Vol 26, PP 322–327.

Illustrative of the phase transfer catalysts of the invention are, for example, organic quaternary ammonium salts, organic arsonium compounds, crown ether compounds, organic phosphonium compounds, tertiary amines and alkylamineoxides. These phase transfer catalysts are further explained definitely as follows.

As the organic quaternary ammonium salts, there are mentioned, tetramethyl ammonium halogenide, tetrapropyl ammonium halogenide, tetrabutyl ammonium halogenide, tetrapentyl ammonium halogenide, benzyltrimethyl ammonium halogenide, methyltriethyl ammonium halogenide, cetyltrimethyl ammonium halogenide, propyltriethyl ammonium halogenide, butyltriethyl ammonium halogenide, pentyltriethyl ammonium halogenide, hexyltriethyl ammonium halogenide, octyltriethyl ammonium halogenide, dodecyltriethyl ammonium halogenide, benzyltriethyl ammonium halogenide, methylbutyl ammonium halogenide, cyclohexyltributyl ammonium halogenide, methyltrioctyl ammonium halogenide, ethyltrioctyl ammonium halogenide, methyltridecyl ammonium halogenide, N-methyl pyridinium halogenide, N-ethyl pyridinium halogenide, N-ethyl pyridinium halogenide, N-propyl pyridinium halogenide, N-octyl pyridinium halogenide and N-benzoyl pyridinium halogenide.

Organic arsonium compounds include tetraphenyl arsonium halogenide and ethyltriphenyl arsonium halogenide. As for the organic phosphonium compounds, there are mentioned for example tetraethyl phosphonium halogenide, benzyltriethyl phosphonium halogenide, dimethyl diphenyl phosphonium halogenide, tetraphenyl phosphonium halogenide, benzyltriphenyl phosphonium halogenide, methyltriphenyl phosphonium halogenide, tetrabutyl phosphonium halogenide, ethyltrioctyl phosphonium halogenide and the like, and compounds in the halogen atom of the above mentioned compounds are substituted with hydroxyl group, bisulphate group ($\ominus SO_3H$), perchloric group ($\ominus ClO_4$) and the like.

Referring to the crown ether compounds, there are mentioned 15-crown-5, 18-crown-6, dibenzo-18-crown-6, dicyclohexyl-18-crown-6, dibenzo-24-crown-8, dicyclohexyl-24-crown-8 and the like.

The tertiary amines include trimethylamine, triethylamine tripropylamine, tributylamine, dimethylbenzylamine, and the like.

Concerning the alkylamine oxides, for example, dimethyldodecylamine oxide and like are usable.

Further, in addition to the above mentioned compounds, the quaternary ammonium hydroxide type anion exchange resin such as Amberlite IRA $(OH^\ominus)_x$ (trademark: product of Tokyo Organic Chemical Industry Co., Ltd.) is usable for the present invention.

As mentioned above, the phase transfer catalysts were explained by reference to concrete examples thereof but any compounds which are effective as the phase transfer catalyst may be used as the same for the present invention. The phase transfer catalysts which are useful for the present invention are not limited to the aforementioned ones.

The quantity of the phase transfer catalyst in the reaction mixture per mole of the mono-substituted acetaldehyde is generally 0.5 mole or less, but in some cases more than 0.5 mole may be required depending on the sort of the organic halide and the reaction conditions. In most cases, the quantity of the phase transfer catalyst in the reaction mixture is, in general, 0.005–0.1 mole under the suitable conditions. The akaline aqueous solutions that may be used in this invention include aqueous solution of hydroxides, carbonate and bicarbonates of alkali metals or alkaline earth metals. Preferably, an aqueous solution of sodium hydroxide or potassium hydroxide is used.

The quantity of the alkali used for the reaction is a molar fraction more than that of the organic halide, because one mole of the halogen ions which are isolated from the organic halide is reacted with one mole of the alkali whereby one mole of the alkali halide is obtained as a by-product, as seen from the aforementioned reaction scheme.

The concentration of the alkaline aqueous solution has in general a tendency that the higher it becomes, the higher is the reaction velocity therefor. The resulting aldehyde dimer gives rise to a self-condensation depending on the kind thereof when the concentration of the alkaline aqueous solution in the reaction mixture is high with the result being that the yield is decreased.

Accordingly, the most suitable conditions should be defined considering the properties of the aldehyde dimer towards the alkaline aqueous solution. Generally the concentration of the alkaline aqueous solution is preferably 10–60 wt% but in some cases it may be applied to the invention outside of this range.

According to the present invention, the β,γ-unsaturated aldehyde may also be obtained by reacting a mixture of a mono-substituted aldehyde, an organic halide and a phase transfer catalyst in an alkaline aqueous solution while being stirred.

However, a solvent suitable for cation solvation promotes the reaction by increasing the concentration of the anion.

Accordingly, it is preferable for adapting the present invention smoothly to charge a solvent in the reaction mixture. As the solvents, any solvents which are inactive to the starting material, aldehyde, the aldehyde dimers, the organic halides, the phase transfer catalysts and the alkaline aqueous solution are available for the present invention.

The preferable solvents include dimethylsulfoxide, acetone, acetonitrile, chloroform, dioxane, benzene, toluene, ethylbenzene, cumene, xylene dichlorobenzene, methylenechloride, ethylenedichloride, ethylether, tetahydrofuran, and carbon tetrachloride.

The faster the stirring velocity is, the more the reaction of the present invention is advanced, because the reaction system is heterogeneous. However, when the stirring velocity reaches a certain velocity or higher, the effect of the stirring velocity on the reaction will be observed no longer.

Further, as the stirring efficiency varies with the structure of the reaction vessel and with the shape of the stirring impeller, the stirring velocity can not be defined in general. It is important for the reaction to establish the stirring conditions so as to give good stirring effect to the reaction mixture. Generally, when the resulting product is further kept with stirring after the reaction is over, the obtained β,γ-unsaturated aldehydes are apt to polymerize, thus forming compounds having high boiling points. The stirring conditions shall be established considering this matter.

The reaction temperature is in general 0°–200° C., perferably 10°–150° C.

When the reaction temperature is too low, the aldol condensation of the aldehyde dimer is preferentially occurs, with the result being that the yield of the final product will be remarkably reduced. On the contrary, when the reaction temperature is too high, the resulted β,γ- unsaturated aldehydes are apt to polymerize, thus forming compounds having high boiling points.

Then, the reaction temperature must be determined considering the reactivity with these aldehydes and organic halides.

It is preferable to carry out the reaction at higher temperature or in an alkaline aqueous solution of high concentration, because aldehyde dimers having high molecular weight are more stable against alkali than aldehyde dimers having low molecular weight. According to the present invention, high purity β,γ- unsaturated aldehydes can be produced by a one step reaction with ease and at a high yield and can economize supplemental materials such as alkali and solvents.

PREFERRED EMBODIMENTS OF THE INVENTION

EXAMPLE 1.

Into a four necked round bottom one liter flask there were charged 95 g of 50 wt% aqueous solution of sodium hydroxide, 70 ml of benzene, and 5 g of tetra-n-butyl ammonium iodide. Into the resulting mixture, a mixture of 200 g of propionaldehyde and 140 g of p-methylbenzyl chloride were added to 70° C. for hours.

The contents of the flask were allowed to continue the reaction at a temperature of 60°–70° C. for 3 hours while being stirred.

The reaction progress was traced from the peaked area of the starting material and the obtained product shown by the gas-liquid chromatography analysis therefor. After the reaction was over, the resulting product was divided into the organic layer and the aqueous layer. The aqueous layer was extracted with ether and the ether layer was added with the organic layer.

The combined layer was washed with water until it became neutral and was followed by a step of drying with anhydrous magnesium sulfate.

The dried layer was subjected to vacuum distillation, thus obtaining 148.7 g of the fraction having a boiling point range of 111°–114° C. at 2 mmHg. This fraction was identified as 2-methyl-2-(4-methylbenzyl)-3-pentenal of purity 95%.

The yield was 78% based on the p-methylbenzyl chloride and was 45.2% based on the propionaldehyde.

EXAMPLE 2

95 g of 50 wt% aqueous solution of sodium hydroxide, 70 ml of toluene and 5 g of tetra-n-butyl ammonium iodide were charged into a four necked round bottom flask of one liter. Into the resulting mixture, a mixture of 200 g of propionaldehyde and 105 g of prenyl chloride were added at 60°–70° C. for 2 hours while being atirred. The contents of the flask were allowed to continue the reaction at a temperature of 60°–70° C. for 4 hours while being stirred well. The tracing of the reaction progress and the treatments of the resulted product were carried out according to the same procedure as that described in Example 1, thus obtaining 110 g of the fraction having a boiling point range of 96°–97.5° C. at 21 mmHg. This fraction was identified as 2,5-dimethyl-2-propenyl-4-hexenal of purity 98%.

The yield was 66% based on the prenyl chloride and 38.4% based on the propionaldehyde.

COMPARATIVE EXAMPLE 1

1725 g of propionaldehyde was added to 500 ml of 4 wt% aqueous solution of sodium hydroxide in a four necked round bottom flask of 5 liter volume at 60°–80° C. for 30 minutes while being stirred.

The obtained organic layer was washed with water and dried with anhydrous magnesium sulphate.

The dried layer was subjected to atmospheric distillation whereby 1100 g of the fraction having a boiling point range of 130°–140° C., was identified as 2-methyl-2-pentenal, was obtained with yield 75%.

Into a four necked round bottom flask of one liter volume were charged 95 g of 50 wt% aqueous solution of sodium hydroxide, 70 ml of toluene and 5 g of tetra-n-butyl ammonium iodide. Further, into the resulting mixture, a mixture of 128 g of the 2-methyl-2-pentenal, which was obtained by the above mentioned procedure and was equivalent to 200 g of propionaldehyde, and 105 g of prenyl chloride was added at 68°–70° C. for 1 hour.

The contents of the flask were allowed to continue the reaction at 68°–70° C. for 5 hours. The tracing of the reaction progress and the treatments of the resulted product were carried out according to the same procedure as that described in Example 1, thus obtaining 91.4 g of the fraction having a boiling point range of 97°–98° C. at 25 mmHg.

The fraction was identified as 2,5-dimethyl-2-propenyl-4-hexenal of purity 96%. The yield was 55% based on the prenylchloride and 42.3% based on the 2-methyl-2-pentenal and 31.7% based on the propionaldehyde.

It was recognized that Example 2 was superior to comparative 1 in the yield and also in consumption of the supplemental materials.

EXAMPLE 3

120 g of 50 wt% aqueous solution of sodium hydroxide, 70 ml of toluene and 1.25g of tetra-n-butyl ammonium iodide were charged into a four necked round bottom flask of one liter.

Into the resulting mixture, a mixture of 198 g of n-butylaldehyde and 127 g of benzyl chloride were added at 70°–75° C. for one and a half hours with stirring. The contents of the flask were allowed to continue the reaction at a temperature of 70°–75° C. for 4 hours with stirring sufficiently.

The tracing of the reaction progress and the treatments of the resulted product after the reaction was over were carried out according to the same procedure as that described in Example 1, thus obtaining 170.6 g of the fraction having a boiling point range of 140°–142° C. at 11 mmHg. This fraction was identified as 2-ethyl-2-benzyl-3-hexenal. The yield was 79% based on the benzyl chloride and 57.5% based on the butyraldehyde.

COMPARATIVE EXAMPLE 2

2160 g of butyraldehyde was added to 500ml of 4 wt% aqueous solution of sodium hydroxide in a four necked round bottom flask of one liter at 60°–80° C. for 40 minutes while being stirred.

The thus obtained organic layer was washed with water and dried with anhydrous magnesium sulfate.

The dried layer was subjected to vacuum distillation whereby 1495 g of the fraction having a boiling point range of 66°–67° C. at 25 mmHg which was identified as 2-ethyl-2-hexenal was obtained with yield 79%.

139 g of the above mentioned 2-ethyl-2-hexenal which was equivalent to 198 g of n-butyraldehyde was reacted with 127 g of benzyl chloride in 120 g of 50% aqueous solution of sodium hydroxide and 70 ml of toluene in the presence of 1.25 g of tetra-n-butyl ammonium iodide according to the same procedure as that described in Example 3 whereby 170 g of the fraction having a boiling point range of 139°–142° C. at 9 mmHg was obtained.

The fraction was identified as 2-ethyl-2-benzyl-3-hexenal of purity 92%. The yield of the final product was 79% based on the benzyl chloride and 71.4% based on the 2-ethyl-2-hexenal and 56.4% based on the butyraldehyde.

EXAMPLE 4

120 g of 50 wt% aqueous solution of sodium hydroxide, 70 ml of cumene and 1 g of tetra-n-butyl ammonium bromide were charged into a four opening flask of one liter having a round bottom.

Into the resulting mixture, a mixture of 198 g of n-butyraldehyde and 91 g of methallyl chloride was added at 71°–76° C. for 1 hour with stirring. The contents of the flask were allowed to continue the reaction at a temperature of 70°–75° C. for 6 hours with stirring. The tracing of the reaction progress and the treatments of the resulted product after the reaction was over, were carried out according to the same procedure as that described in Example 1, thus obtaining 135 g of the fraction having a boiling point of 91°–93° C. at 1 mmHg.

This fraction was identified as 2-ethyl-2-methallyl-3-hexenal of purity 96%. The yield was 75% based on the methallyl chloride and was 54.5% based on the butyraldehyde.

EXAMPLE 5

120 g of 50 wt% aqueous solution hydroxide, 70 ml of benzene and 1.25 g of tetra-n-butyl ammonium iodide were charged into a four opening flask of one liter having a round bottom.

Into the resulting mixture, a mixture of 198 g of n-butyr-aldehyde and 74.5 g of propargyl chloride were added for two hours at a temperature of 45°–50° C. with stirring sufficiently. The contents of the flask were allowed to continue the reaction at a temperature of 45°–48° C. for 4 hours while being stirred.

The tracing of the reaction progress and the treatments of the resulted product were carried out according to the same procedure as that described in Example 1, thus obtaining 77 g of the fraction having a boiling point range of 85°–87° C. at 15 mmHg.

The fraction was identified as 2-ethyl-2-propargyl-3-hexenal of purity 94%. The yield was 47% based on the propargyl chloride and 34.2% based on the butyraldehyde.

COMPARATIVE EXAMPLE 3

139 g of the 2-ethyl-2-hexenal which was obtained in Comparative test 2 was reacted with 74.5g of propargyl chloride according to the same procedure as that described in Example 5 thus obtaining 67.2 g of the fraction have a boiling point range of 84.5°–87° C. at 15 mmHg.

The fraction was identified as 2-ethyl-2-propargyl-3-hexenal of purity 93%.

The yield of the final product was 41% based on the propargyl chloride and 29.2% based on the butyraldehyde.

EXAMPLE 6

120 g of 50 wt% aqueous solution of sodium hydroxide, 70 ml of toluene and 1.25 g of tetra-n-butyl ammonium iodide were charged into a four opening flask of one liter having a round bottom. Into the resulting mixture, a mixture of 198 g of n-butyraldehyde and 121 g of allyl bromide were added for two hours at a temperature of 65°–70° C. with stirring. The contents of the flask were allowed to continue the reaction at a temperature of 65°–75° C. for 4 hours with stirring fully. The tracing of the reaction progress and the treatments of the resulted products were carried out according to the same procedure as described in Example 1, whereby 89.6 g of the fraction having a boiling point range of 86°–89° C. at 15 mmHg is obtained. The fraction was identified as 2-ethyl-2-allyl-3-hexenal of purity 95%.

The yield of the final product was 54% based on the allyl bromide and 39.3% based on the butyraldehyde.

The embodiment of the invention in which an exclusive property or privilege is claimed are defined as follows;

1. A process for preparing $\beta, \gamma$- unsaturated aldehyde having the formula

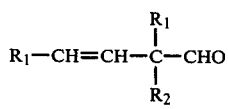

wherein $R_1$ is selected from the group consisting of alkyl having 1 to 12 carbon atoms, phenyl,

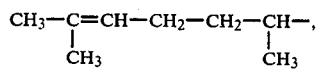

$CH_2=CH(CH_2)_7-$ and cyclohexyl, and $R_2$ is selected from the group consisting of allyl, crotyl, methyallyl, 2-methylcrotyl, prenyl, 2,3-dimethylcrotyl, 2-heptenyl, 4,4-dimethyl-2-pentenyl, 2-chloroallyl, 3-chloroallyl, 2-bromoallyl, 2-methyl-3-chloroallyl, 3-chloro-2-pentenyl, cinnamyl, geranyl, propynyl, 2-butynyl, 1-butynyl, 2-pentynyl, 2-hexynyl, 2-heptynyl, 1-phenylpropynyl, 4-chloro-2-butynyl, benzyl, methylphenylmethyl, ethylphenylmethyl, isopropylphenylmethyl, fluorophenylmethyl, chlorophenylmethyl, bromophenylmethyl, iodophenylmethyl, hydroxyphenylmethyl, methoxymethylphenyl, phenoxyphenylmethyl, nitrophenylmethyl, cyanophenylmethyl, acetylphenylmethyl and α-methylnaphthalene, which comprises: admixing and vigorously stirring, at a temperature of from 10° to 150° C., (A) an aldehyde having the formula $R_1-CH_2-CHO$, with (B) a halide having the formula $R_2X$, wherein X is halogen, at a molar ratio of A:B in the range of from 2:1 to 10:1, in an aqueous solution of an alkaline material selected from the group consisting of alkali metal and alkaline earth metal hydroxides, carbonates and bicarbonates wherein the amount of said alkaline material is a molar excess relative to B, and in the presence of an organic quaternary ammonium salt effective as a phase transfer catalyst and present in an amount of not more than 0.5 mole per mole of A and effective to catalyse the reaction of A and B whereby to form said β, γ-unsaturated aldehyde, and recovering said β, γ-unsaturated aldehyde from the reaction mixture.

2. A process according to claim 1 wherein said quaternary ammonium salt is selected from the group consisting of tetramethyl ammonium halogenide, tetrapropyl amonium halogenide, tetrabutyl ammonium halogenide, tetrapentyl ammonium halogenide, benzyltrimethyl ammonium halogenide, methyltriethyl ammonium halogenide, cetyltrimethyl ammonium halogenide propyltriethyl ammonium halogenide, butyltriethyl ammonium halogenide, pentyltriethyl ammonium halogenide, hexyltriethyl ammonia halogenide, octyltriethyl ammonium halogenide, dodecyltriethyl ammonium halogenide, benzyltriethyl ammonium halogenide, methylbutyl ammonium halogenide, methylbutyl ammonium halogenide, cyclohexyltributyl ammonium halogenide, methyltrioctyl ammonium halogenide, ethyltrioctyl ammonium halogenide, methyltridecyl ammonium halogenide, N-methyl pyridinium halogenide, N-ethyl pyridinium halogenide, N-propyl pyridinium halogenide, N-octyl pyridinium halogenide and N-benzoyl pyridinium halogenide.

3. A process according to claim 1 wherein said quaternary ammonium salt is selected from the group consisting of tetra-n-butyl ammonium iodide and tetra-n-butyl ammonium bromide.

4. A process according to claim 1 in which said aqueous solution of alkaline material is an aqueous solution of sodium hydroxide or potassium hydroxide having a concentration of from 10 to 60 percent by weight.

5. A process according to claim 1 in which the reaction mixture also contains an organic solvent which is inactive to the other ingredients of the reaction mixture.

6. A process according to claim 1 in which said aldehyde A is propionaldehyde, said halide B is p-methylbenzyl chloride and said organic quaternary ammonium salt is tetra-n-butyl ammonium iodide.

7. A process according to claim 1 in which said aldehyde A is propionaldehyde, said halide B is prenyl chloride and said organic quaternary ammonium salt is tetra-n-butyl ammonium iodide.

8. A process according to claim 1 in which said aldehyde A is n-butyraldehyde, said halide B is benzyl chloride and said organic quaternary ammonium salt is tetra-n-butyl ammonium iodide.

9. A process according to claim 1 in which said aldehyde A is n-butyraldehyde, said halide B is methallyl chloride and said organic quaternary ammonium salt is tetra-n-butyl ammonium bromide.

10. A process according to claim 1 in which said aldehyde A is n-butyraldehyde, said halide B is propargyl chloride and said organic quaternary ammonium salt is tetra-n-butyl ammonium iodide.

11. A process according to claim 1 in which said aldehyde A is n-butyraldehyde, said halide B is allyl chloride and said organic quaternary ammonium salt is tetra-n-butyl ammonium iodide.

* * * * *

UNITED STATES PATENT AND TRADEMARK OFFICE
CERTIFICATE OF CORRECTION

PATENT NO. : 4 196 151
DATED : April 1, 1980
INVENTOR(S) : Shuji Suyama et al

It is certified that error appears in the above-identified patent and that said Letters Patent are hereby corrected as shown below:

Column 9, line 50;  after "halogenide" (second occurrence) insert a comma (,).
Column 10, line 3;  change "ammonia" to ---ammonium---.
Column 10, line 6;  delete "methylbutyl ammonium" (second occurrence).
line 7;  delete "halogenide," (first occurrence).

Signed and Sealed this

Fifteenth Day of July 1980

[SEAL]

Attest:

SIDNEY A. DIAMOND

Attesting Officer          Commissioner of Patents and Trademarks